United States Patent [19]

Ferrand et al.

[11] Patent Number: 4,552,878
[45] Date of Patent: Nov. 12, 1985

[54] BENZO- AND THIENO-TRIAZINE-1,2,3 ONES-4

[75] Inventors: Gérard Ferrand, Lyons; Hervé Dumas, Villefontaine; Michel Bayssat, Charbonnieres; Jean-Claude Depin, Lyons, all of France

[73] Assignee: Lipha, Lyonnaise Industrielle Pharmaceutique, Paris, France

[21] Appl. No.: 534,173

[22] Filed: Sep. 19, 1983

[30] Foreign Application Priority Data

Sep. 22, 1982 [FR] France ................... 82 15934

[51] Int. Cl.$^4$ .................. C07D 253/08; C07D 403/06; A61K 31/53
[52] U.S. Cl. .................... 514/243; 544/183; 544/184
[58] Field of Search ............... 544/183, 184; 424/249; 514/243

[56] References Cited

U.S. PATENT DOCUMENTS 2,489,359 11/1949 Wolf et al. .................... 544/183
3,316,262 4/1967 Hasspacher et al. ............ 544/183
3,808,318 4/1974 Kathawala ..................... 544/183

FOREIGN PATENT DOCUMENTS 1926076 12/1970 Fed. Rep. of Germany ..
1578785 7/1969 France .
1280941 7/1972 United Kingdom .

Primary Examiner—John M. Ford
Attorney, Agent, or Firm—Browdy and Neimark

[57] ABSTRACT

This invention relates to benzo- and thieno-triazine-1,2,3 ones-4 represented by the formula

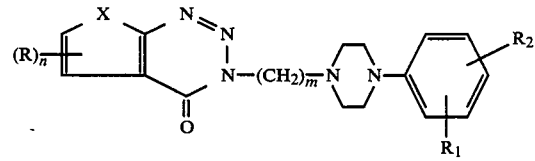

in which m is 2, 3 or 4, X is the vinylene group —CH=CH— or a sulfur atom; $R_1$ and $R_2$ can be alike or different and are hydrogen, halogen, a lower alkyl radical, lower alkoxy radical or trifluoromethyl radical; when X is —CH—CH— n is 0, 1 or 2 and R is hydrogen, halogen, a lower alkyl radical, lower alkoxy radical or nitro group; when X is a sulfur atom, R is hydrogen or constitutes a —(CH$_2$)$_4$— chain between the two open positions of the thiophenic ring. The compounds are useful as antidepressant drugs.

6 Claims, No Drawings

BENZO- AND THIENO-TRIAZINE-1,2,3 ONES-4

FIELD OF THE INVENTION

This invention relates to [phenyl-4 piperazinyl-1]-3 alcoyl-3-3H-benzo- and thieno-triazine-1,2,3 ones 4, processes that make it possible to prepare them and their application in the therapeutic field.

BACKGROUND OF THE INVENTION

The possible role of 5-hydroxytryptamine (5-HT) in the etiology of depression is of great interest in the study of selective inhibitors of its neuronal recapture. Compounds have been discovered that exhibit this property and that can be used in the treatment of depressive states and mental disorders.

Dichloro-6,8 (phenyl-4 piperazinomethyl)-3-3H-benzo-triazine-1,2,3 one-4 is known by the work described in French Pat. No. 1,578,785 of N. V. Philips' Gloeioampenfabrieken. as a depressant of the central nervous system. In German Pat. No. 1,926.076 A. Stachel and R. Beverke describe a [hydroxy-2 (phenyl-4 piperazinyl-1)-3 propyl]-3 trimethoxy-6,7,8-3H-benzotriazine-1,2,3 one-4 among a series of ($\alpha$-amino $\beta$-hydroxypropyl)-3-3H-benzotriazine-1,2,3 ones-4 that are used as intermediates for cardiovascular medicines.

SUMMARY OF THE INVENTION

The compounds which are the objects of the invention are represented by the general formula I

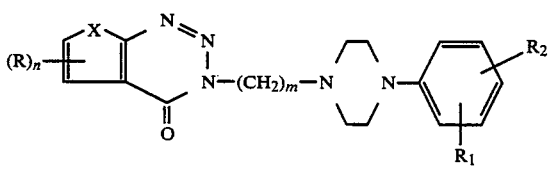

in which m is 2, 3 or 4, and X is the vinylene group —CH=CH— or a sulfur atom. When X=—CH=CH—, R can occupy any position on the aromatic ring and can be hydrogen, a halogen, a lower alkyl radial, a lower alkoxy radical or nitro group, n being 0, 1, or 2; when X is a sulfur atom, R is hydrogen or constitutes a (—CH$_2$—)$_4$ chain between the two open positions of the thiophenic cycle. R$_1$ and R$_2$ can be alike or different and are hydrogen, a halogen, a lower alkyl radical, a lower alkoxy radical, or trifluoromethyl radical. R$_1$ and R$_2$ can occupy any position on the aromatic ring.

The term lower applied to an alkyl or alkoxy group indicates that the group can be straight or branched and that it can comprise 1 to 3 carbon atoms.

The compounds in the formula in which R$_1$ and R$_2$ are hydrogen or a halogen constitute a particularly advantageous class.

Acceptable pharmaceutical salts are an integal part of the invention. They can be salts prepared either from inorganic acids such as hydrochloric acid, hydrobromic acid, sulfuric acid, phosphoric acid, or from organic acids such as tartaric acid, citric acid, acetic acid, maleic acid, fumaric acid, oxalic acid, and methanesulfonic acid.

The compounds of the invention can be prepared according to at least one of the following methods:

(a) a triazine-1,2,3 one-4 of formula II

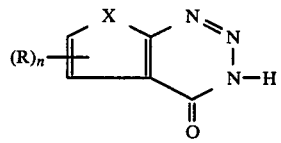

is alkylated by a derivative of formula III

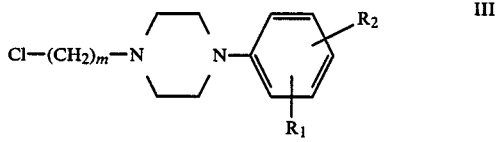

In formulas II and III, X, R, R$_1$, R$_2$, m and n have the previously given meanings. The reaction is performed in an inert solvent in the presence of an alkaline agent. The preferred solvents are alkanols of low molecular weight, especially acetonitrile and N N-dimethylformamide. The bases used can be alcoholates, hydroxides or alkaline carbonates. The temperature can vary between ambient temperature and the boiling temperature of the solvent used. The reaction time is generally between 1 and 12 hours.

The triazine-1,2,3 ones-4 of formula II constitute a known class of compounds of several of those used have already been described. Those which are new have been prepared according to usual techniques, by diazotization either of the amides or the methyl or ethyl esters of the corresponding anthranilic acids—for example see A. Weddige and H. Finger, *J. Prakt. Chem* 35,262 (1882). Also, several of the derivatives of formula III used are known. The others have been prepared by alkylation of a 1-phenyl piperazine suitably substituted by 1-bromo-$\omega$-chloroalcane according to the techniques described, for example, see by J. Bourdais [*Bull. Soc. Chim. France* 3246 (1968] or by C. B. Pollard et coll. [*J. Org. Chem.* 24,764 (1959)].

(b) a benzotriazine-1,2,3 one-4 of general formula IV

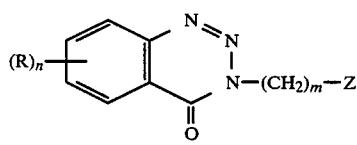

is condensed on a 1-phenyl piperazine suitably substituted, of general formula V

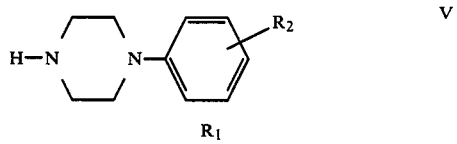

In formulas IV and V, R, R$_1$, R$_2$, m and n have the previously given meanings. Z represents a group that can be easily removed by an amine and preferably is a halogen atom or a tosyl (Ts) or mesyl (Ms) group. The reaction is performed in an inert solvent such as acetonitrile, N,N-dimethylformamide or an alkanol of low molecular weight. It can be performed with either excess of phenylpiperazine V or in the presence of a hydroxide or an alkaline carbonate. The temperature can vary between ambient temperature and the boiling temperature of the solvent used. The reaction time is generally between 10 and 60 hours. The derivatives IV are obtained from the corresponding hydroxylated derivatives of general formula VI

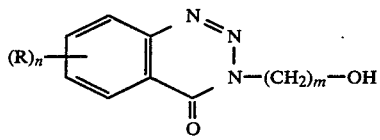

in which R and n have the previously given meanings, according to standard techniques. Thus the derivatives IV for which Z=Cl are obtained by treating the alcohols VI with thionyl chloride. The derivatives IV for which Z=Ts or Z=Ms are obtained by treating the alcohols VI with paratoluenesulfonyl chloride or methanesulfonyl chloride, either in pyridine or in a solvent such as methylene chloride or chloroform in the presence of a base such as pyridine or triethylamine.

The derivatives VI wherein m=3 are new intermediate compounds that are part of the invention. They can be prepared according to the following methods:

(α) treatment of the diazonium salt of a derivative of the formula VII

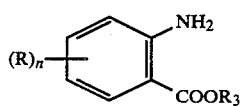

in which R and n have the same meanings as previously and $R_3$ is a lower alkyl radical, with the 3-amino propanol.

(β) treatment of an isatoic anhydride of general formula VIII

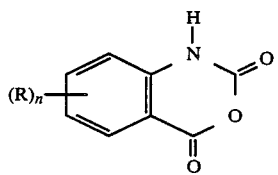

with the 3-amino propanol to lead to a derivative of general formula IX

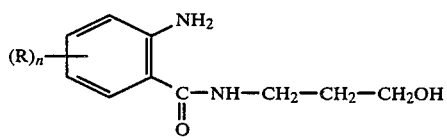

which is cyclized, without intermediate isolation, by diazotization by an alkaline nitrite. In formulas VIII and IX, R and n have the previously given meanings.

It has been found that the compounds represented by formula I have remarkable properties which effect the central nervous system in such a way that they are useful in human medicine in the treatment of depressive states and mental disorders.

This mood-modifying activity can be determined by standardized tests such as the potentiation of the central effects of 5-hydroxytryptophan (5-HPT). This potentiation objectifying the axonal blocking of the reabsorption of the seratonin at the serotoninergic nerve ends was studied by the method described by T. M. Pugsley and X. Lippmann [*Experentia* 33, 57 (1977)]: Swiss mice are treated I.P (intraperitonally) with the compounds of the study, 30 minutes before receiving 300 mg/kg of 5-HTP intraperitoneally. The mice are observed 30 min later, for 1 min, during which the following sterotyped movements are classified: extension of the hind paws, trembling, excitement, head shaking.

The effective doses 50 ($ED_{50}$) obtained for some products of the invention and the one obtained for Trazodone hydrochloride (2-[3-[4-(3-chlorophenyl)-1-piperazinyl]propyl]-1,2,4-triazolo[4,3-a]pyridin-3 (2H)-one hydrochloride) taken as a standard are given in Table I:

TABLE I

| PRODUCTS | Potentiation of the 5-HTP $ED_{50}$ DE50 (mg/kg/I.P.) |
|---|---|
| Trazodone Hydrochloride | 20 |
| Example 1 | 3 |
| Example 6 | 12 |
| Example 9 | 5 |
| Example 10 | 14 |
| Example 11 | 8 |
| Example 15 | 9 |
| Example 16 | 11 |
| Example 19 | 10 |
| Example 20 | 8 |
| Example 23 | 3 |
| Example 27 | 8 |
| Example 28 | 5 |
| Example 29 | 12 |

The products of the invention demonstrates a slight toxicity. The lethal doses 50 ($LD_{50}$) determined on the Swiss mice orally for some of the most active derivatives are given in Table II.

TABLE II

| PRODUCT | $LD_{50}$ ORALLY (mg/kg) |
|---|---|
| Trazodone Hydrochloride | 650 |
| Example 1 | >3200 |
| Example 10 | 1500 |
| Example 11 | 1000 |
| Example 20 | >3200 |
| Example 23 | 1060 |

This application also has as its object the application of the compounds I as medicines and especially antidepressant drugs. These medicines can be administered orally in the form of tablets, sugar-coated tablets or, capsules or rectally in the form of suppositories. The active principle is associated with various pharmaceutically compatible excipients. The daily dosage can vary from 0.010 g to 0.5 g of g of active principle depending on the age of the patient and the seriousness of the treated mental state. Given below, by way of nonlimiting example, are some pharmaceutical formulations.

| Compositions of possibly coated 100 mg tablet: | |
|---|---|
| active principle | 10 mg |
| lactose | 40 mg |
| wheat starch | 37 mg |
| gelatin | 2 mg |
| alginic acid | 5 mg |
| talc | 5 mg |

-continued

| | |
|---|---|
| magnesium stearate | 1 mg |
| Composition of a capsule: | |
| active principle | 10 mg |
| lactose | 32 mg |
| wheat starch | 25 mg |
| talc | 2.5 mg |
| magnesium stearate | 0.5 mg |
| Composition of a 3 g supository: | |
| Active principle | 20 mg |
| semi-sythetic triglycerides | |
| q.s.a. for | 3 g |

DESCRIPTION OF THE PREFERRED EMBODIMENTS OF THE INVENTION

The following examples illustrate the invention in a nonlimiting way. In the data of nuclear magnetic resonance (N.M.R.) the following abbreviations have been used: s for singlet, t for triplet and quint for quintuplet.

EXAMPLE 1

[[(chloro-3 phenyl)-4 piperazinyl-1]-3 propyl]-3-3H-benzotriazine-1,2,3 one-4, hydrochloride.

A mixture of 90.5 g (0.615 mole) of 3H-benzotriazine-1,2,3 one-4 [prepared according to A. Weddige and H. Finger, *J. Prakt. Chem.* 35, 262 (1887)], 168 g (0.615 mole) of 1-3-chloro phenyl)-4-3-chloro propyl)piperazine [prepared according to *J. Bourdais Bull. Soc. Chim. France* 3246, (1968)], 86 g (0.615 mole) of potassium carbonate and 3200 cc of acetonitrile is brought to reflux for 6 hours. After cooling, the inorganic products are removed by filtering and the filtrate is concentraded to dryness under reduced pressure. The residue is filtered over silica (¼ hexane-ethyl acetate eluent). The concentration of the eluate supplies the [[(chloro-3 phenyl)-4 piperazinyl-1]-3 propyl]-3-3H-benzotriazine-1,2,3, one-4. It is purified by recrystallization in ethanol. Yield: 156.1 g (66%), melting point=92°–94° C.

| Percentage Analysis $C_{20}H_{22}ClN_5O$ (M = 383.88) | | | | |
|---|---|---|---|---|
| | C % | H % | Cl % | N % |
| Calculated | 62.57 | 5.78 | 9.24 | 18.24 |
| Found | 62.70 | 5.63 | 9.49 | 18.00 |

I.R. $\bar{\nu}(C{=}O) = 1685$ cm$^{-1}$.

N.M.R. (CDCl$_3$ $\delta$=2.1 (2H, quint); 2.4–2.8 (6H, complex mass); 2.9–3.3 (4H, complex mass); 4.6 (2H, t) 6.4–7.3 (4H, complex mass); 7.6–8.6 (4H, complex mass).

The [[chloro-3 phenyl)-4 piperazinyl-1]-3 propyl]-3-3H-benzotriazine-1,2,3 one-4 hydrochloride is prepared by dissolving the base in ethanol, adding 10N hydrochloric acid, then evaporating to dryness. It is purified by recrystallization in ethanol. Melting point=201°–203° C.

| Percentage analysis $C_{20}H_{23}Cl_2N_5O$ (M = 420.33) | | | | |
|---|---|---|---|---|
| | C % | H % | Cl % | N % |
| Calculated | 57.15 | 5.51 | 16.66 | 16.87 |
| Found | 57.23 | 5.46 | 16.52 | 16.72 |

I.R. $\bar{\nu}(C{=}O) = 1670$ cm$^{-1}$.

N.M.R. (DMSO d$_6$ $\delta$=2.2–2.8 (2H, complex mass); 2.8–4.2 (10H, complex mass); 4.5 (2H,t); 6.7–8.4 (4H, complex mass); 7.6–8.4 (4H, complex mass); 12.7 (1H, peak interchangeable with D$_2$O).

EXAMPLE 2

[[(Chloro-3 phenyl)-4 piperazinyl-1]-3 propyl]-3-3H-benzotriazine-1,2,3 one-4

A solution of 170.2 g (0.623 mole) of 1-3-chlorophenyl-4-(3-chloropropyl) piperazine in 230 cc of N,N-dimethylformamide is added drop by drop, at 80° C., to a mixture of 91.7 g (0.623 mole) of 3H-benzotriazine-1,2,3 one-4 of 87 g (0.623 mole) of potassium carbonate and 1400 cc of N,N-dimethylformamide. The heating is continued 1 hour after the end of the addition. The inorganic products are then filtered and the filtrate concentrated to dryness under reduced pressure. The residue is filtered on silica. The evaporation of the eluate supplies the [[chloro-3 phenyl)-1 piperazinyl-1]-3 propyl]-3-3H-benzotriazine-1,2,3 one-4 identical with that obtained in example 1. Yield: 38.5 g (58%), Melting point=92°–94° C. (ethanol).

EXAMPLE 3

[[(Chloro-3 phenyl)-4 piperazinyl-1]-3 propyl]-3-3H-benzotriazine-1,2,3 one-4

(a) (Hydroxy-3 propyl)-3-3H-benzotriazine-1,2,3 one-4

53.8 g (0.33 mole) of isatoic anhydride are added by portions to a solution of 32.3 g (0.43 mole) of 3-amino propanol in 120 cc of water. The temperature rises spontaneously to 35° C. The mixture is brought to reflux for 15 min. After cooling, the reactive medium is acidified by 130 cc of 33% hydrochloric acid, then between 0° and 2° C. a solution of 27.6 g (0.4 mole) of sodium nitrite is added drop by drop into 75 cc of water. The reactive medium is stirred for 30 min at this temperature, basified by ammonia and extracted several times with methylene chloride with salting out of the aqueous phase with sodium chloride. The organic extracts are concentrated in a vacuum. The oily residue obtained is solidified by triturating in a mixture of hexane and benzene. The (hydroxy-3 propyl)-3-3H-benzotriazine-1,2,3 one-4 is purified by recrystallization in a hexene-ethyl acetate mixture. Yield: 75% Melting point=74°–76° C.

| Percentage analysis $C_{10}H_{11}N_3O_2$ (M = 205.21) | | | |
|---|---|---|---|
| | C % | H % | N % |
| Calculated | 58.53 | 5.40 | 20.48 |
| Found | 58.71 | 5.48 | 20.09 |

I.R. $\bar{\nu}(C{=}O) = 1660$ cm$^{-1}$. $\bar{\nu}(OH) = 3400$ cm$^{-1}$.

N.M.R. (CDCl$_3$) $\delta$=2.2 (2H, quint); 3.2 (1H, peak interchangeable with D$_2$O); 3.7 (2H, t); 4.7 (2H,t); 7.5–8.6 (4H, complex mass).

Another method of synthesis is also possible:

A solution of 27.4 g (0.4 mole) of sodium nitrite in 200 cc of water is added drop by drop between 0° and 2° C., to a mixture of 50 g (0.33 mole) of methyl anthranilate, 92.6 cc (1 mole) of 33% hydrochloric acid and 300 cc of water. After 1 hour of stirring, always between 0° and 2° C., 49.6 g (0.66 mole) of 3-amino propanol are added drop by drop. The stirring is continued for 1 more hour. The reactive medium is allowed to return to ambient temperature, then basified by ammonia. The treatment is continued as described above. Yield: 62%

(b) (Chloro-3 propyl)-3-3H-benzotriazine-1,2,3 one-4

4.1 cc (56 m. moles) of thionyl chloride are added to a solution of 9.5 g (46 m. moles) of (hydroxy-3 propyl)-3-3H-benzotriazine-1,2,3,one-4 in 110 cc of chloroform. After 4 hours at ambient temperature, the insoluble material is filtered. The filtrate is concentrated under reduced pressure and the residue is solidified in hexane. It is purified by recrystallization in ethanol.

Yield: 51%, Melting point=70°-72° C.

| Percentage analysis C$_{10}$H$_{10}$ClN$_3$O (M = 223.66) | | | | |
| --- | --- | --- | --- | --- |
| | C % | H % | Cl % | N % |
| Calculated | 53.70 | 4.51 | 15.85 | 18.79 |
| Found | 53.76 | 4.50 | 15.35 | 18.59 |

I.R. $\bar{\nu}(C=O)=1680$ cm$^{-1}$.

(c) [[Chloro-3 phenyl-4 piperazinyl-1]-3 propyl]-3-3H-benzotriazine-1,2,3 one-4, hydrochloride A solution of 7.8 g (35 m. moles) of (chloro-3 propyl)-3-3H-benzotriazine-1,2,3 one-4 13 g (66 m. moles) of (chloro-3 phenyl)-1 piperazine and 100 mg of potassium iodine in 70 cc of acetonitrile is brought to reflux for 34 hours. The 1-(3-chloro phenyl) piperazine hydrochloride is filtered. The filtrate is concentrated under reduced pressure and the residue purified by filtration on silica (⅓ hexane-ethyl acetate eluent). The eluate is concentrated in a vacuum and the residue dissolved in ethanol. 6.9 cc of 33% hydrochloric acid are added to this solution. After concentration to drying, under reduced pressure, the [[(chloro-3 phenyl)-4 piperazinyl-1]-3 propyl]-3-3H-benzotriazine-1,2,3 one-4 hydrochloric is recrystallized in ethanol. Yield: 6.2 g (42%), Melting point=201°-203° C. The product is identical with that obtained in example 1.

EXAMPLE 4

[[(Chloro-3 phenyl)-4 piperazinyl-1]-3-3H]-benzotriazine-1,2,3 one-4

(a) [(Methyl-4 benzensulfonyl)-3 propyl]-3-3H-benzotriazine-1,2,3 one-4

20 g (105 m. moles) of 4-methyl benzenesulfonyl chloride are added by portions to a solution, cooled to 0° C., of 10.7 g (52 m. moles) of (hydroxy-3 propyl)-3-3H-benzotriazine-1,2,3 one-4 (prepared as described in example 3) in 250 cc of pydidine. The reactive medium is stirred 4 hours at 0° C. then left 24 hours at this temperature. It is then poured into 21 g of ice water. The precipitate formed is filtered, washed in water and dried. It is recrystallized in a mixture of hexane and ethyl acetate. Yeild: 12.6 g (67%), Melting point=76°-77° C.

| Percentage analysis C$_{17}$H$_{17}$N$_3$O$_4$S (M = 359.40) | | | | |
| --- | --- | --- | --- | --- |
| | C % | H % | N % | S % |
| Calculated | 56.81 | 4.77 | 11.69 | 8.92 |
| Found | 56.76 | 4.80 | 11.67 | 8.88 |

I.R. $\bar{\nu}(C=O)=1680$ cm$^{-1}$.

N.M.R. (DMSO d$_6$) δ=2.2 (2H, quint); 2.4 (3H,s); 4.2 (2H, t); 4.5 (2H,t); 7.4-7.9 (4H, 2d); 7.9-8.5 (4H, complex mass).

(b) [[(Chloro-3 phenyl)-4 piperazinyl-]-3 propyl]-3-3H-benzotriazine-1,2,3 one-4

A mixture of 7.2 g (20 m moles) of [(methyl-4 benzensulfonyl)-3 propyl]-3-3H-benzotriazine-1,2,3 one-4, 3.9 g (20 m moles) of 1-3(3-chloro phenyl)piperazine, 3.1 g (22 m moles) of potassium carbonate and 50 cc of N,N-dimethylformamide is stirred for 8 hours at ambient temperature, then 1 hour at 80° C. After cooling, the reactive medium is poured into 500 cc of water. The precipitate is filtered and recrystallized in ethanol.

4.0 g (yield: 52%) of [[(chloro-3 phenyl)-4 piperazinyl-1]-3 propyl]-3-3H-benzotriazine-1,2,3 one-4 identical with that obtained in the preceding examples are obtained.

EXAMPLE 5

[[(Chloro-3 phenyl)-4 piperazinyl-1]-3 propyl]-3-3H-benzotriazine-1,2,3 one-4

(a) (Methanesulfonyl-3 propyl)-3-3H-benzotriazine-1,2,3 one-4

16.2 g (0.16 mole) of triethylamine are added at 0° C. to a solution of 22.1 g (0.017 mole) of (hydroxy-3 propyl)-3-3H-benzotriazine-1,2,3 one-4 in 535 cc of methylene chloride, then drop by drop, still at 0° C., 15.9 g (0.139 mole) of methanesulfonyl chloride are added. The stirring is continued for 20 min, then the reactive medium is poured over the ice. The organic phase is decanted, washed with a saturated solution of sodium bicarbonate and dried on sodium sulfate. After evaporation of the solvent, the residue is solidified in hexane and recrystallized in a mixture of hexane and ethyl acetate.

Yield: 23.6 g (78%), Melting point=102°-103° C.

| Percentage analysis C$_{11}$H$_{13}$N$_3$O$_4$S (M = 283.30) | | | | |
| --- | --- | --- | --- | --- |
| | C % | H % | N % | S % |
| Calculated | 46.63 | 4.62 | 14.83 | 11.32 |
| Found | 46.66 | 4.60 | 14.74 | 11.35 |

I.R. $\bar{\nu}(C=O)=1660$ cm$^{-1}$.

N.M.R. (CDCl$_3$) δ=2.2 (2H, quint); 2.9 (3H, s); 4.2 (2H,t); 4.5 (2H, t); 7.4-8.3 (4H, complex mass)

(b) [[Chloro-3 phenyl)-4 piperazinyl-1]-3 propyl]-3-3H-benzotriazine-1,2,3 one-4

A mixture of 11.3 g (40 m. moles) of (methanesulfonyl-3 propyl)-3-3H-benzotriazine-1,2,3 one-4, 7.8 g (40 m. moles) of 1-(3-chloro phenyl)piperazine, 6.2 g (44 m. moles) of potassium carbonate and 100 cc of N,N-dimethylformamide is stirred at ambient temperature for 2 hours, then at 90° C. for 6 hours. After cooling, the reactive medium is taken up with water and extracted with ether. The organic phase is concentrated and the residue recrystallized in ethanol. There are obtained 3.7 g (yield: 24%) of [[(chloro-3 phenyl)-4 piperazinyl-1]-3 propyl]-3-3H-benzotriazine-1,2,3 one-4 identical with that obtained in the preceding examples.

EXAMPLE 6

[[(Chloro-2 phenyl)-4 piperazinyl-1]-3 propyl]3-3H-benzotriazine-1,2,3 one 4, hydrochloride By proceeding as example 1, from 4.4 g (30 m. moles) of 3H-benzotriazine-1,2,3 one-4, 8.2 g (30 m. moles) of 1-(2-chloro phenyl)-4-(3-chloro propyl)piperazine [prepared according to C. B. Pollard et coll. *J. Org. Chem.*

24,764 (1959)], 8.4 g (60 m. moles) of potassium carbonate and 150 cc acetonitrile, there are obtained 6.1 g (yield: 48%) of [[(chloro-2 phenyl)-4 piperazinyl-1]-3 propyl]-3-3H-benziotriazine-1,2,3 one-4 hydrochloride, Melting point 232°–234° C. (ethanol).

| Percentage analysis $C_{20}H_{23}Cl_2N_5O$ (M = 420.33) | | | | |
|---|---|---|---|---|
| | C % | H % | Cl % | N % |
| Calculated | 57.15 | 5.51 | 16.87 | 16.66 |
| Found | 56.97 | 5.40 | 16.88 | 16.49 |

I.R. $\overline{\nu}(C=O) = 1690$ cm$^{-1}$.

EXAMPLE 7

[[(Trifluoromethyl-3 phenyl)-4 piperazinyl-1]-3 propyl]-3-3H-benzotriazine-1.2.3. one-4, hydrochloride By proceeding as in example 3 it is obtained from 6.2 g (28 m. moles) of (chloro-3 propyl)-3-3H-benzotriazine-1,2,3 one-4  12 g (46 m. moles) of 1-(3-trifluoromethyl phenyl)piperazine hydrochloride [prepared according to A. F. Ash et coll. British patent 948,765; C.A. 60, 12019a (1964)], 23.4 g (170 m. moles) potassium carbonate, 100 mg potassium iodide and 80 cc of acetonitrile.

Yield: 5.0 g (39%), Melting point=208°–210° C. (ethanol).

| Percentage analysis $C_{21}H_{23}ClF_3N_5O$ (M = 453.89) | | | | | |
|---|---|---|---|---|---|
| | C % | H % | Cl % | F % | N % |
| Calculated | 55.57 | 5.11 | 7.81 | 12.56 | 15.43 |
| Found | 55.68 | 5.06 | 7.48 | 12.65 | 15.33 |

I.R. $\overline{\nu}(C=O) = 1680$ cm$^{-1}$.

EXAMPLE 8

[[(Chloro-4 phenyl)-4 piperazinyl-1]-3 propyl]-3-3H-benzotriazine-1,2,3, one 4 hyrochloride By proceeding as in example 3 it is obtained from 5.6 g (25 m. moles) of (chloro-3 propyl)-3-3H-benzotriazine-1,2,3 one-4, 9.8 g (50 m. moles) of 1-(4-chloro phenyl)piperazine, 7.1 g (51 m. moles) of potassium carbonate 100 mg potassium iodide and 80 cc of acetonitrile. Yield: 6.0 g (57%), Melting point=232°–234° C. (ethanol).

| Percentage analysis $C_{20}H_{23}Cl_2N_5O$ (M = 420.33) | | | | |
|---|---|---|---|---|
| | C % | H % | Cl % | N % |
| Calculated | 57.15 | 5.51 | 16.87 | 16.66 |
| Found | 56.95 | 5.60 | 16.97 | 16.80 |

I.R. $\overline{\nu}(C=O) = 1680$ cm$^{-1}$.

EXAMPLE 9

[[(Methyl-2 phenyl)-4 piperazinyl-1]-3 propyl]-3-3H-benzotriazine-1,2,3 one-4 hydrochloride By proceeding as in example 1, it is obtained from 6.4 g (43.5 m. moles) of 3H-benzotriazine-1,2,3 one-4, 11 g (43.5 m. moles) of 1-(3-chloro proply)-4-2(methyl phenyl)piperazine [prepared according to C. B. Pollard et coll. J. Org. Chem. 24, 764 (1959)], 12.2 g (87 m. moles) of potassium carbonate and 220 cc of acetonitrile. Yield: 9.4 g (54%) Melting point—215°–217° C. (ethanol).

| Percentage analysis $C_{21}H_{26}ClN_5O$ (M = 399.92) | | | | |
|---|---|---|---|---|
| | C % | H % | Cl % | N % |
| Calculated | 63.07 | 6.55 | 8.87 | 17.51 |
| Found | 63.21 | 6.64 | 9.18 | 17.42 |

I.R. $\overline{\nu}(C=O) = 1685$ cm$^{-1}$.

EXAMPLE 10

[[(Fluoro-3phenyl)-4 piperazinyl-1]-3 propyl]-3H-benzotriazine-1,2,3 one-4, hydrochloride By proceeding as in example 1, it is obtained from 4.6 g (31 m. moles) of 3H-benzotriazine-1,2,3-one-4, 8 g (31 m. moles) of 1-(3-chloro propyl)-4-(3-fluoro phenyl)piperazine, 8.7 g (63 m. moles) of potassium carbonate and 155 cc acetonitrile. Yield: 7.1 g (56%), Melting point=225°–226° C.

| Percentage analysis $C_{20}H_{23}ClFN_5O$ (M = 403.88) | | | | | |
|---|---|---|---|---|---|
| | C % | H % | Cl % | F % | N % |
| Calculated | 59.47 | 5.74 | 8.78 | 4.70 | 17.34 |
| Found | 59.75 | 5.75 | 8.51 | 4.73 | 17.35 |

I.R. $\overline{\nu}(C=O) = 1665$ cm$^{-1}$.

The 1-(3-chloropropyl)-4-(3-fluorophenyl piperazine used is prepared in the following manner: 32 g (203 m. moles) of 1-bromo-3-chloropropane are added drop by drop to a mixture of 12.2 g (67.7 m. moles) Of 1-(3-fluorophenyl piperazine [prepared according to D. R. Maxwell and W. R. Wragg, English Pat. No. 943,739, C.A. 60, 5522c (1964)], 9.4 g (68 m. moles) of potassium carbonate and 135 cc of N,N-dimethylformamide. The stirring is continued for 9 hours at ambient temperature. The inorganic products are then removed by filtration, then the filtrate is concentrated under reduced pressure. The residue is dissolved in ether, the solution washed with a saturated solution of sodium chloride, then dried on sodium sulfate. The evaporation of the ether supplies an oil which is distilled (boiling$_1$=137°–140°). The 1-(3-chloropropyl)-4-(3-fluorophenyl)piperazine is obtained in the form of an oil that is crystallized in hexane. Yield: 11.6 g (67%), Melting point=48°–49° C.

| Percentage analysis $C_{13}H_{18}ClN_2$ (M = 256.75) | | | | | |
|---|---|---|---|---|---|
| | C % | H % | Cl % | F % | N % |
| Calculated | 60.81 | 7.07 | 13.81 | 7.40 | 10.91 |
| Found | 61.16 | 7.14 | 13.90 | 7.45 | 10.94 |

EXAMPLE 11

[(Phenyl-4 piperazinyl-1)-3 propyl]-3-3H-benzotriazine-1,2,3 one-4 hydrochloride By proceeding as in example 1, there is obtained from 8.8 g (60 m. moles) of 3H-benzotriazine-1,2,3 one-4, 14.3 g (60 m.moles) of 1-(3-chloropropyl-4-phenyl)piperatine, 16.6 g (120 m. moles) of potassium carbonate and 300 cc acetonitrile. Yield: 12.7 g (55%), Melting point=205°–207° C. (ethanol).

| Percentage analysis $C_{20}H_{24}ClN_5O$ (M = 385.89) | | | | |
|---|---|---|---|---|
| | C % | H % | Cl % | N % |
| Calculated | 62.26 | 6.27 | 9.19 | 18.15 |

-continued

| Percentage analysis $C_{20}H_{24}ClN_5O$ (M = 385.89) | | | | |
|---|---|---|---|---|
| | C % | H % | Cl % | N % |
| Found | 62.18 | 6.42 | 9.12 | 18.22 |

I.R. $\overline{\nu}(C=O) = 1680$ cm$^{-1}$.

EXAMPLE 12

[[(Methoxy-2 phenyl)-4 piperazinyl-1]-3 propyl]-3-3H-benzotriazine-1,2,3 one-4

By proceeding as in example 1, it is obtained from 4.2 g (29 m. moles) of 3H-benzotriazine-1,2,3 one-4, 7.7 g (29 m. moles) of 1-(3-chloro propyl)4-(2-methoxyphenyl)piperazine [prepared according to J. Bourdais Bull. Soc. Chim. France 3246, (1968)], 8.0 g (58 m. moles) potassium carbonate and 145 cc of acetonitrile. Yield: 5.9 g (54%), Melting point=86°-88° C. (hexane-ethyl acetate).

| Percentage analysis $C_{21}H_{25}N_5O_2$ (M = 379.45) | | | |
|---|---|---|---|
| | C % | H % | N % |
| Calculated | 66.47 | 6.64 | 18.46 |
| Found | 66.56 | 6.65 | 18.28 |

I.R. $\overline{\nu}(C=O) = 1690$ cm$^{-1}$.

EXAMPLE 13

[[(Methyl-3 phenyl)-4 piperazinyl-1]-3 propyl]-3-3H-benzotriazine-1,2,3 one-4

By proceeding as in example 1, it is obtained from 5.9 g (40 m. moles) of 3H-benzotriazine-1,2,3 one-4 of 10.1 g (40 m. moles) of 1-(3-chloro propyl)-4-(3-methyl phenyl)piperazine, 5.6 g (40 m. moles) potassium carbonate and 100 cc of N,N-dimethylformamide. Yield: 9.0 g (62%), Melting point=72°-73° C. (pentane-ethyl acetate)

| Percentage analysis $C_{21}H_{25}N_5O$ (M = 363.45) | | | |
|---|---|---|---|
| | C % | H % | N % |
| Calculated | 69.39 | 6.93 | 19.27 |
| Found | 69.38 | 6.93 | 19.40 |

I.R. $\overline{\nu}(C=O) = 1690$ cm$^{-1}$.

The 1-(3-chloropropyl)-4(3-methylphenyl)piperazine used is prepared in the following manner: 21.3 g (136 m. moles) of 1-bromo-chloropropane are added quickly, with stirring, to a mixture of 20 g (113 m. moles) of 1-(3-methyl phenyl)piperazine [prepared according to C. B. Pollard and T. Wicker Jr. J. Am. Chem. Soc. 76, 1853 (1954)], 18.7 g (136 m. moles of potassium carbonate and 110 cc of N,N-dimethylformamide. The stirring is continued for 5 hours at ambient temperature. The inorganic products are then filtered and filtrate concentrated under reduced pressure. The residue is dissolved in ether, the solution is washed with a saturated solution of sodium chloride, then dried on sodium sulfate. After evaporation of the ether the residue is distilled. Boiling 2-3=156°-160° C., Yield: 14.7 g (52%). N.M.R. (CDCl$_3$) δ=2.0 (2H, quint); 2.3 (2H, s); 2.4-2.8 (6H, complex mass); 3.1-3.4 (4H, complex mass) 3.6 (2H, t); 6.6-6.9 (3H, complex mass); 7.0-7.4 (1H, complex mass).

EXAMPLE 14

[[(Methyl-4 phenyl)-4 piperazinyl-1]-3 propyl]-3-3H-benzotriazine-1,2,3 one-4

By proceeding as in example 1, it is obtained from 4.4 g (30 m. moles) of 3H-benzotriazine-1,2,3 one-4, 7.6 g (30 m. moles) of 1-(3-chloro propyl)-4-(4-methyl phenyl)piperazine, 8.4 g (60 m. moles) of potassium carbonate and 150 cc of acetonitrile. Yield: 6.8 g (62%), Melting point=86°-87° C. (hexane-ethyl acetate)

| Percentage analysis $C_{21}H_{25}N_5O$ (M = 363.45) | | | |
|---|---|---|---|
| | C % | H % | N % |
| Calculated | 69.39 | 6.93 | 19.27 |
| Found | 69.24 | 6.94 | 19.22 |

I.R. $\overline{\nu}(C=O) = 1690$ cm$^{-1}$.

The 1-(3-chloro propyl)-4-(4-methyl phenyl)piperazine used is obtained by proceeding as in example 13, from 13.2 g (84 m. moles) of 1-bromo-3-chloro-propane, 12.3 g (70 m. moles) of 1-(4-methyl phenyl)piperazine [prepared according to C. B. Pollard and T. H. Wicker Jr. J. Am. Chem. Soc. 76, 1853 (1954)], 11.6 g (84 m. moles) of potassium carbonate and 70 cc of N,N-dimethylformamide, Yield: 7.6 g (43%), boiling 1-3=150°-160° C.

EXAMPLE 15

[[(Methoxy-3 phenyl)-4 piperazinyl-1]-3 propyl]-3-3H-benzotriazine-1,2,3 one-4

By proceeding as in example 1, it is obtained from 5.1 g (35 m. moles of 3H-benzotriazine-1,2,3 one-4, 9.4 g (35 m. moles) of 1-(3-chloro propyl)-4-(3-methoxyphenyl)-piperazine, 9.7 g (70 m. moles) of potassium carbonate and 200 cc of acetonitrile. Yield: 8.2 g (62%), Melting point =63°-65° C. (pentane-ethyl acetate)

| Percentage analysis $C_{21}H_{25}N_5O_2$ (M = 379.45) | | | |
|---|---|---|---|
| | C % | H % | N % |
| Calculated | 66.47 | 6.64 | 18.46 |
| Found | 66.18 | 6.56 | 18.34 |

I.R. $\overline{\nu}(C=O) = 1690$ cm$^{-1}$.

The 1-(3-chloropropyl)-4-(3-methoxyphenyl)piperazine used is prepared by proceeding as in example 13, from 11.8 g (75 m. moles) of 1-bromo-3-chloropropane, 12.0 g (62.5 m. moles) of 1-(3-methoxyphenyl)piperazine [prepared according to P. C. Jain et coll. J. Med. Chem. 10, 812 (1967)], 10.4 g (75 m. moles) of potassium carbonate and 65 cc of N,N-dimethylformamide. Yield: 9.4 g (56%), boiling 2-3=175°-190° C.

EXAMPLE 16

[[(Methoxy-4 phenyl)-4 piperazinyl-1]-3propyl]-3-3H-benzotriazine-1,2,3 one-4

By proceeding as in example 1, there is obtained from 4.1 g (28 m. moles) of 3H-benzotriazine-1,2,3 one-4, 7.5 g (28 m. moles) of 1-(3-chloropropyl)-4-(4-methoxyphenyl)piperazine [prepared according to J. Bourdais, Bull. Soc. Chim. France 3245, 1968)], 7.8 g (56 m. moles) of potassium carbonate and 140 cc of acetonitrile. Yield: 4.5 g (42%), Melting point=111°-113° C. (hexane-ethyl acetate).

| Percentage analysis C₂₁H₂₅N₅O₂ (M = 379.45) | | | |
|---|---|---|---|
| | C % | H % | N % |
| Calculated | 66.47 | 6.64 | 18.46 |
| Found | 66.71 | 6.70 | 18.30 |

I.R. $\bar{\nu}(C=O) = 1685$ cm$^{-1}$.

EXAMPLE 17

Chloro-6[[(chloro-3 phenyl)-4 piperazinyl-1]-3 propyl]-3-3H-benzotriazine-1,2,3 one-4 hydrochloride Obtained according to the series of reactions described in Example 3.

STAGE A

Chloro-6 (hydroxy-3 propyl)-3-3H-benzotriazine-1,2,3 one-4

48.9 g (0.25 mole) of 5-chloroisatoic anhydride is added by portions to a solution of 24.8 g (0.33 mole) of 3-amino-1-propanol in 90 cc of water. The mixture is brought to reflux for 15 min. After cooling the reactive medium is acidified with 100 cc of 33% hydrochloric acid, then there is added, at between 0° and 2° C., a solution of 21 g (0.3 mole) of sodium nitrite in 60 cc of water. The reactive medium is stirred for 30 min at this temperature, then basified with ammonia. The precipitate obtained is filtered, dried and recrystallized in a mixture of hexane and ethyl acetate. Yield: 44.5 g (74%), Melting point=102°-104.5° C.

| Percentage analysis C₁₀H₁₀ClN₃O₂ (M = 239.66) | | | | |
|---|---|---|---|---|
| | C % | H % | Cl % | N % |
| Calculated | 50.11 | 4.21 | 14.79 | 17.53 |
| Found | 49.96 | 4.12 | 14.52 | 17.40 |

I.R. $\bar{\nu}(C=O) = 1670$ cm$^{-1}$. $\bar{\nu}(OH) = 3420$ cm$^{-1}$.

N.M.R. (CDCl₃) δ=2.2 (2H, quint); 2.8 (1H, s. interchangeable with D₂O); 3.8 (2H, t); 4.7 (2H,t); 7.8-8.5 (3H, complex mass).

STAGE B (Chloro-6 (chloro-3 propyl)-3-3H-benzotriazine-1,2,3 one-4

From 24 g (0.1 mole) of chloro-6 (hydroxy-3 propyl)-3-3H-benzotriazine-1,2,3 one-4, 8.7 cc (0.12 mole) of thionyl chloride and 400 cc of chloroform, 10 g of product are obtained. Yield: 39%, Melting point=102°-105° C. (ethanol).

I.R. $\bar{\nu}(C=O) = 1660$ cm$^{-1}$.

N.M.R. (CdCl₃) δ=2.4 (2H, quint); 4.2 (2H, t); 4.7 (2H,t); 7.8-8.6 (3H, complex mass).

STAGE C

Chloro-6 [[(chloro -3 phenyl)-4 piperazinyl-1]-3propyl]-3-3H-benzotriazine-1,2,3 one-4, hydrochloride A mixture of 3.2 g (12 m. moles) of chloro-6 (chloro-3 propyl)-3-3H-benzotriazine-1,2,3 one-4, 6.5 g (24 m. moles) of 1-(3-chlorophenyl)piperazine hydrochloride, 10.2 g (72 m. moles) of potassium carbonate, 50 mg of potassium iodide and 50 cc of acetonitrile is brought to reflux for 38 hours. After cooling, the reactive medium is diluted with 200 cc of water and extracted with methylene chloride. The organic solution is concentrated to drying and the residue purified by filtration on silica (⅓ hexane-ethyl acetate eluant). The concentration of the eluate under reduced pressure supplies a residue which is dissolved in ethanol. To this solution there are added 1.5 cc of 33% hydrochloric acid and evaporated to dryness. The chloro-6[[(chloro-3 phenyl)-4 piperazinyl-1]-3 propyl]-3-3H-benzotriazine-1,2,3 one-4 hydrochloride is recrystallized in ethanol. Yield: 1.0 g (18%), Melting point=228°-230.5° C.

| Percentage analysis C₂₀H₂₂Cl₃N₅O (M = 454.79). | | | | |
|---|---|---|---|---|
| | C % | H % | Cl % | N % |
| Calculated | 52.82 | 4.88 | 23.39 | 15.40 |
| Found | 52.65 | 4.76 | 23.47 | 15.34 |

I.R. $\bar{\nu}(C=O) = 1670$ cm$^{-1}$.

EXAMPLE 18

Chloro-6 [[(chloro-3 phenyl)-4 piperazinyl-1]-3 propyl]-3-3H-benzotriazine 1,2,3 one-4 hydrochloride By proceeding as in example 1, from 3.6 (20 m. moles) of chloro-6-3H-benzotriazine-1,2,3 one-4 [prepared according to S. M. Gadekar and E. Ross, *J. Org. Chem.* 26 613 (1961)], 5.5 g (20 m. moles) of 1-(3-chlorophenyl)-4-(3-chloropropyl) piperazine, 5.6 g (40 m. moles) potassium carbonate and 100 cc of acetonitrile, there are obtained 5.6 g (yield: 62%) of the desired product, identical with that obtained in example 17.

EXAMPLE 19

Chloro-7 [[(chloro-3 phenyl)-4 piperazinyl-1]-3 propyl]-3-3H-benzotriazine-1,2,3 one-4 hydrochloride Obtained by proceeding as in example 1 from 6.4 g (35 m. moles) of chloro-7-3H-benzotriazine-1,2,3 one-4 [prepared according to S. M. Gadekar and E. Ross, *J. Org. Chem.* 26, 613 (1961)], 9.6 g (35 m. moles) of 1-(3-chlorophenyl-4-(3-chloropropyl)piperazine, 9.9 g (70 m. moles) of potassium carbonate and 175 cc of acetonitrile. Yield: 8.7 g (55%), Melting point=218°-220° C. (ethanol).

| Percentage analysis C₂₀H₂₂Cl₃N₅O (M = 454.79) | | | | |
|---|---|---|---|---|
| | C % | H % | Cl % | N % |
| Calculated | 52.82 | 4.88 | 23.39 | 15.40 |
| Found | 52.86 | 5.05 | 23.33 | 15.49 |

I.R. $\bar{\nu}(C=O) = 1680$ cm$^{-1}$.

EXAMPLE 20

[[(Chloro-3 phenyl)-1 piperazinyl-1]-3 propyl]-3 methyl-6-3H-benzotriazine-1,2,3 one-4, hydrochloride Obtained by proceeding as in example 1, from 7.6 g (47 m. moles) of methyl-6-3H-benzotriazine-1,2,3 one-4, 12.9 g (47 m. moles) of 1-(3-chlorophenyl)-4-(3-chloropropyl)piperazine, 13.0 g (94 m. moles) of potassium carbonate and 245 cc of acetonitrile. Yield: 10.8 g (53%), Melting point=232°-234° C. (ethanol-DMF).

| Percentage analysis C₂₁H₂₅Cl₂N₅O (M = 434.36) | | | | |
|---|---|---|---|---|
| | C % | H % | Cl % | N % |
| Calculated | 58.06 | 5.80 | 16.33 | 16.13 |
| Found | 57.95 | 5.78 | 16.41 | 16.12 |

I.R. $\bar{\nu}(C=O) = 1670$ cm$^{-1}$.

The methyl-6-3H-benzotriazine-1,2,3 one-4 was prepared in the following manner: a solution of 5.5 g (79 m. moles) of sodium nitrite in 55 cc of water is added drop by drop, between 0° and 2° C. to a mixture of 10 g (66 m. moles) of 2-amino-5-methyl-benzamide [prepared according to K. Wasti et Coll. Synthesis 570 (1974)], 49.5 cc 33% hydrochloric acid and 115 cc of water. The stirring is continued at this temperature, 1 hour after the end of the addition. The reactive medium is then basified with 35 cc of 34% ammonia. The precipitate obtained is filtered, washed with water, dried, then recrystallized in ethanol. Yield: 7.6 g (60%), Melting point=219°–220° C.

| Percentage analysis $C_8H_7N_3O$ (M = 161.16) | | | |
|---|---|---|---|
|  | C % | H % | N % |
| Calculated | 59.62 | 4.38 | 26.07 |
| Found | 59.35 | 4.42 | 26.06 |

I.R. $\overline{\nu}(C=O) = 1665$ cm$^{-1}$.

EXAMPLE 21

[[(Chloro-3 phenyl)-4 piperazinyl-1]-3 propyl]-3 methoxy-6-3H-benzotriazine-1,2,3 one-4 hydrochloride Obtained by proceeding as in Example 1, from 9 g (51 m. moles) of methoxy-6-3H-benzotriazine-1,2,3 one-4 [prepared according to J. G. Archer et coll. *J. Chem. Soc. Perkin Trans.* 1 1169 (1973)], 13.9 g (51 m. moles) of 1-(3-chlorophenyl)-4-(3-chloropropyl)piperazine, 14.2 g (103 m moles) of potassium carbonate and 155 cc of acetonitrile. Yield: 8.3 g (36%), Melting point=211°–213° C. (ethanol).

| Percentage analysis $C_{21}H_{25}Cl_2N_5O$ (M = 450.36) | | | | |
|---|---|---|---|---|
|  | C % | H % | Cl % | N % |
| Calculated | 56.00 | 5.60 | 15.75 | 15.55 |
| Found | 55.73 | 5.77 | 15.95 | 15.26 |

I.R. $\overline{\nu}(C=O) = 1675$ cm$^{-1}$.

EXAMPLE 22

[[(Chloro-3 phenyl)-4 piperazinyl-1]-3 propyl]-3 dimethoxy-6.7-3H-benzotriazine-1,2,3 one-4, hydrochloride Obtained by proceeding as in example 1, from 5.8 g (28 m. moles) of dimethoxy-6.7-3H-benzotriazine-1,2,3 one-4 [prepared according to F. G. Kathawal, U.S. Pat. No. 3,678,166], 7.7 g (28 m..moles) of 1-(3-chlorophenyl-4-(3-chloropropyl piperazine, 3.9 g (28 m. moles of potassium carbonate and 140 cc of acetonitrile. Yield: 4.6 g (37%). Melting point=235°–237° C. (ethanol).

| Percentage analysis $C_{22}H_{27}Cl_2N_5O_3$ (M = 443.93) | | | | |
|---|---|---|---|---|
|  | C % | H % | Cl % | N % |
| Calculated | 55.00 | 5.67 | 14.76 | 14.58 |
| Found | 54.64 | 5.80 | 14.73 | 14.40 |

I.R. $\overline{\nu}(C=O) = 1675$ cm$^{-1}$.

EXAMPLE 23

[[(Chloro-3 phenyl)-4-piperazinyl-1]3 propyl]-3-3H-thieno[2,3-d]triazine-1,2,3 one-4 hydrochloride Obtained by proceeding as in example 1, from 4.1 g (27 m. moles) of 3H-thieno[2,3-d]triazine-1,2,3 one-4 [prepared according to F. Sauter and W. Deinhammer *Monatsch. Chem.* 104, 1586 (1973)], 7.4 g (27 m. moles) of 1-(3-chlorophenyl)-4-(3-chloropropyl)piperazine, 4.2 g (30 m. moles) of potassium carbonate and 130 cc of acetonitrile. Yield: 4.9 g (43%), Melting point=220°–224° C. (ethanol).

| Percentage analysis $C_{18}H_{21}Cl_2N_5OS$ (M = 426.37) | | | | | |
|---|---|---|---|---|---|
|  | C % | H % | Cl % | N % | S % |
| Calculated | 50.70 | 4.97 | 16.63 | 16.43 | 7.52 |
| Found | 50.46 | 4.96 | 16.37 | 16.13 | 7.25 |

I.R. $\overline{\nu}(C=O) = 1695$ cm$^{-1}$.

EXAMPLE 24

[[(Chloro-3 phenyl)-4 piperazinyl-1]-3 propyl]-3 tetrahydro-5,6,7,8-3H-benzo [1] thieno [2,3-d] triazine-1,2,3 one-4 hydrochloride Obtained by proceeding as in example 1, from 5.2 g (25 m. moles) of tetrahydro-5,6,7,8-3H-benzo [1] thieno (2,3-d] triazine-1,2,3 one-4 [prepared according to F. Sauter and W. Deinhammer *Monatsh. Chem.* 104, 1586 (1973)]6.8 g (25 m. moles) of 1-(3-chlorophenyl-4-(3-chloropropyl)piperazine, 7.0 g (50 m. moles) of potassium carbonate and 125 cc of acetonitrile. Yield: 7.0 g (63%), Melting point=163°–164.5° C. (ethanol).

| Percentage analysis $C_{22}H_{27}Cl_2N_5OS$ (M = 480.46) | | | | | |
|---|---|---|---|---|---|
|  | C % | H % | Cl % | N % | S % |
| Calculated | 54.99 | 5.67 | 14.76 | 14.58 | 6.67 |
| Found | 54.81 | 5.70 | 14.58 | 14.64 | 6.79 |

I.R. $\overline{\nu}(C=O) = 1670$ cm$^{-1}$.

EXAMPLE 25

[[(Chloro-3 phenyl)-4 piperazinyl-1]-3 propyl]-3 nitro-6-3H-benzotriazine-1,2,3 one-4 hydrochloride Obtained by proceeding as in example 1, from 10 g (52 m. moles) of nitro-6-3H-benzotriazine-1,2,3 one-4 [prepared according to J. Adamson et coll. *J. Chem. Soc. C,* 981 (1971)], 14.8 g (54 m. moles) (chloro -3 phenyl)-1 (chloro-3 propyl)-4 piperazine, 7.2 g (52 m. moles) potassium carbonate and 260 cc of acetonitrile. Yield: 4.5 g (19%), Melting point=239°–241° C. (ethanol).

| Percentage analysis $C_{20}H_{22}Cl_2N_6O_3$ (M = 465.34) | | | | |
|---|---|---|---|---|
|  | C % | H % | Cl % | N % |
| Calculated | 51.62 | 4.77 | 15.24 | 18.06 |
| Found | 51.58 | 4.84 | 15.12 | 18.32 |

I.R. $\overline{\nu}(C=O) = 1690$ cm$^{-1}$.

EXAMPLE 26

Chloro-8 [[Chloro-3)phenyl-4 piperazinyl-1]-3-propyl]-3-3H-benzotrazine-1,2,3 one-4 hydrochloride Obtained by proceeding as in example 1, from 7.8 g (43 m. moles) of chloro-8-3H-benzotriazine-1,2,3 one-4 [prepared according to the technique described in: C. A. 68, 114665e (1968)], 11.8 g (43 m. moles) of 1-(3-chlorophenyl)-4-(3-chloropropyl)piperazine, 12 g (87 m. moles) potassium carbonate and 130 cc of acetonitrile. Yield: 7.4 g (38%), Melting point=225°–227° C. (ethanol-DMF).

| Percentage analysis $C_{20}H_{22}Cl_3N_5O$ (M = 454.79) | | | | |
| --- | --- | --- | --- | --- |
| | C % | H % | Cl % | N % |
| Calculated | 52.82 | 4.88 | 23.39 | 15.40 |
| Found | 53.11 | 4.91 | 23.39 | 15.39 |

I.R. $\bar{\nu}(C=O) = 1675$ cm$^{-1}$.

EXAMPLE 27

[[(Chloro-3 fluoro-4 phenyl)-4 piperazinyl-1]-3 propyl]-3-3H-benzotriazine-1,2,3 one-4 hydrochloride Obtained by proceeding as in example 1, from 5.3 g (36 m. moles) of 3H-benzotriazine-1.2,3 one-4, 9.7 g (36 m. moles) of 1-(3-chloro-4-fluorophenyl-4-(3-chloropropyl piperazine (36 m. mole of potassium carbonate and 100 cc of N,N-dimethylformamide. Yield: 8.4 g (53%), Melting point=234°–235° C. (ethanol-DMF).

| Percentage analysis $C_{20}H_{22}Cl_2FN_5O$ (M = 438.33) | | | | | |
| --- | --- | --- | --- | --- | --- |
| | C % | H % | Cl % | F % | N % |
| Calculated | 54.80 | 5.06 | 16.18 | 4.33 | 15.98 |
| Found | 54.70 | 5.03 | 15.93 | 4.30 | 16.25 |

I.R. $\bar{\nu}(C=O) = 1680$ cm$^{-1}$.

The 1-(3-chloro-4-fluorophenyl)-4-(3-chloropropyl)-piperazine used is obtained by proceeding as in example 13, from 8.3 (53 m. moles) of 1-bromo 3-chloropropane, 9.4 g (44 m. moles) of 1-(3-chloro-4-fluorophenyl)piperazine [prepared according to B. W. Horrom and H. B. Wright, U.S. Pat. No. 3,637,705; C.A. 76, 113256a (1972)], 7.3 g (53 m. moles) of potassium carbonate and 45 cc of N,N-dimethylformamide.

Yield: 9.7 g (81%), boiling 1.5=160°–170° C.

EXAMPLE 28

Chloro-6[(phenyl-4 piperazinyl-1)-3 propyl]-3-3H-benzotriazine-1,2,3 one-4 dihyrochloride Obtained by proceeding as in example 1, from 6 g (33 m. moles) of chloro-6-3H-benzotriazine-1,2,3 one-4, 7.9 g (33 m. moles) of 1-(3-chloropropyl)-4-phenyl piperazine, 9.1 g (66 m. moles) of potassium carbonate and 165 cc of acetonitrile. Yield: 6.8 g (45%), Melting point=223°–225° C. (ethanol)

| Percentage analysis $C_{20}H_{24}Cl_3N_5O$ M = 456.80 | | | | |
| --- | --- | --- | --- | --- |
| | C % | H % | Cl % | N % |
| Calculated | 52.58 | 5.30 | 23.29 | 15.33 |
| Found | 52.63 | 5.32 | 23.37 | 15.39 |

I.R. $\bar{\nu}(C=O) = 1680$ cm$^{-1}$.

EXAMPLE 29

[[(Dimethoxy-3,4 phenyl)-4 piperazinyl-1]-3 propyl]-3-3H-benzotriazine-1,2,3 one-4 dihydrochloride A mixture of 6.9 g (47 m. moles) of 3H-benzotriazine-1,2,3 one-4, 14 g (47 m. moles) of 1-(3-chloropropyl)-4-(3H-dimethoxyphenyl)piperazine, 6.5 g (47 m. moles) of potassium carbonate and 130 cc of N,N-dimethylformamide is brought to 80° C. for 1 hour. After cooling, the inorganic products are filtered and the filtrate concentrated to dryness under reduced pressure. The residue is chromatographed on a silica column (95:5 ethyl acetate-methanol eluent). 47 g of a solid that melts at 94°–95° C. is obtained. This solid is dissolved in 250 cc of ethanol. 2.6 cc of 10N hydrochloric acid are added to the solution obtained and it is evaporated to dryness under reduced pressure. The recrystallization of the residue in a mixture of ethanoldimethylformamide supplies the dihydrochloride of the desired product. Yield: 3.2 g (14%), Melting point=204°–206° C.

| Percentage analysis $C_{22}H_{29}Cl_2N_5O_3$ M = 482.40 | | | | |
| --- | --- | --- | --- | --- |
| | C % | H % | Cl % | N % |
| Calculated | 54.77 | 6.06 | 14.70 | 14.52 |
| Found | 54.74 | 6.11 | 14.75 | 14.57 |

I.R. $\bar{\nu}(C=O) = 1695$ cm$^{-1}$.

The 1-(3-chloropropyl-4-(3,4-dimethoxyphenyl)piperazine is prepared in the following manner: 11.5 g (70.2 m. moles) of 1-bromo-3-chloropropane are added quickly with stirring to a mixture of 13 g (58.5 m. moles) of 1-(3,4-dimethoxyphenyl)piperazine [prepared according to P. C. Jain et coll. *J. Med. Chem.* 10, 812 (1967)] and 9.7 g (70.2 m. moles) of potassium carbonate in 60 cc of N,N-dimethylformamide. The stirring is continued for 4 hours 30 min at ambient temperature. The inorganic products are then filtered and the filtrate concentrated to dryness under reduced pressure. The residue is dissolved in ether and the solution obtained washed with water, then dried on sodium sulfate. After evaporation of the ether, there is obtained 14 g (yield 80%) of 1-(3-chloropropyl)-4-(3,4-dimethoxyphenyl)-piperazine that is used without any other purification.

EXAMPLE 30

[[(Chloro-3 phenyl)-4 piperazinyl-1]-3 propyl]-3 dichloro-6,8-3H-benzotriazine-1,2,3-one-4 hydrochloride Obtained as in example 29 above from 450 mg (2.1 m. moles) of dichloro-6,8-3H-benzotriazine-1,2,3 one-4 [prepared according to S. M. Gadekar and E. Ross *J. Org. Chem.* 26, 613 (1961)], 570 mg (2.1 m. moles) of 1-(3-chlorophenyl)-4-(3-chloropropyl)piperazine, 290 mg (2.1 m. moles) of potassium carbonate and 20 cc of N,N-dimethylformamide. Yield: 0.15 g (15%), Melting point=256°–259° C. (Ethanol-DMF).

| Percentage analysis $C_{20}H_{21}Cl_4N_5O$ M = 489.24 | | | | |
| --- | --- | --- | --- | --- |
| | C % | H % | Cl % | N % |
| Calculated | 49.10 | 4.33 | 28.99 | 14.32 |
| Found | 48.90 | 4.28 | 28.68 | 13.99 |

I.R. $\bar{\nu}(C=O) = 1685$ cm$^{-1}$.

EXAMPLE 31

[[(Chloro-3 phenyl)-4 piperazinyl-1]-2 ethyl]-3-3H-benzotriazine-1,2,3 one-4 hydrochloride A mixture of 10.5 g (50 m. moles) of (chloro-2 ethyl-3-3H-benzotriazine-1,2,3 one-4 [prepared according to K. Hasspacher and G. Ohnacker, U.S. Pat. No. 3,316,262 C.A. 67, 64445q (1967)], 27 g (100 m. moles) of 1-(3-chlorophenyl)piperazine hydrochloride, 42.3 g (300 m. moles) of potassium carbonate, 0.1 g of potassium iodide and 150 cc of acetonitrile is brought to reflux for 40 hours. The mixture is diluted with 500 cc of water and filtered. The solid thus isolated is purified by filtration on silica (ethyl acetate eluent). The [[(chloro-3 phenyl)-4-piperzinyl-1]-2 ethyl]-3-3H-benzotriazine-1,2,3 one-4 -melting at 154°–157° C. is obtained. It is dissolved in ethanol. There are added 9.8 cc of 10N hydrochloric acid to this solution and then it is evaporated to dryness under reduced pressure. The recrystallization of the residue in an ethanol-DMF mixture supplies the desired hydrochloride.

Yield: 11.5 g (57%), Melting point=225°–227° C.

| Percentage analysis $C_{19}H_{21}Cl_2N_5O$ M = 406.31 | | | | |
|---|---|---|---|---|
| | C % | H % | Cl % | N % |
| Calculated | 56.16 | 5.21 | 17.45 | 17.24 |
| Found | 55.07 | 5.45 | 17.32 | 17.01 |

EXAMPLE 32

[[(Methoxy-2 phenyl)-4 piperazinyl-1]-2 ethyl]-3-3H-benzotriazine-1,2,3 one-4 hydrochloride A solution of 7.7 g (40 m. moles) of 1-(2-methoxyphenyl)piperazine in 20 cc of N,N-dimethylformamide is added drop by drop to a mixture of 13.8 g (40 m. moles) of [methyl-4 benzenesulfonyl)-2 ethyl]-3-3H-benzotriazine-1,2,3 one-4 [prepared according to A. J. Barker et coll. *J. Chem. Soc. Perkin* 1, 1979 2203] and 6.1 g (44 m. moles) of potassium carbonate in 100 cc of N,N-dimethylformamide. The reactive medium is stirred 1 hour at ambient temperature, and then brought to 80° C. for 2 hours 30 min. After cooling, the inorganic products are removed by filtration and the filtrate concentrated to dryness under reduced pressure. The residue is taken up by a mixture of water and methylene chloride. The organic phase is washed with water, dried on sodium sulfate and concentrated in a vacuum. The residue is dissolved in 250 cc of ethanol. There are added 9,4 cc of 10N hydrochloric acid to this solution and then it is evaporated to dryness under reduced pressure. The [[methoxy-2 phenyl)-4- piperazinyl-1]-2 ethyl]-3-3H-benzotriazine-1,2,3 one-4 hydrochloride obtained is purified by recrystallization in an ethanol-DMF mixture. Yield: 8.7 g (54%), melting point=225°–227° C.

| Percentage analysis $C_{20}H_{24}ClN_5O_2$ M = 401.89 | | | | |
|---|---|---|---|---|
| | C % | H % | Cl % | N % |
| Calculated | 59.77 | 6.02 | 8.82 | 17.43 |
| Found | 59.60 | 6.12 | 8.74 | 17.32 |

I.R. $\bar{\nu}(C=O) = 1680$ cm$^{-1}$.

EXAMPLE 33

[[(Chloro-3 phenyl)-4 piperazinyl-1]-4 butyl-9 -3-3H-benzotriazine-1,2,3 one-4

(a) [(Hydroxy-4 butyl)-1]-3-3H-benzotriazine-1,2,3 one-4

A solution of 32.7 g (0.30 mole) of 4-chloro-1-butanol in 235 cc of N,N-dimethylformamide is added drop by drop, at ambient temperature, to a mixture of 27.7 g (0.188 mole) of 3H-benzotriazine-1,2,3 one-4 and 28 g (0.207 mole) of potassium carbonate in 235 cc of N,N-dimethylformamide. The reactive medium is brought to 80° C. for 3 hours. The inorganic products are filtered and the filtrate concentrated to dryness under reduced pressure. The residue is filtered on silica (1:4 hexane-ethyl acetate eluent). 24.2 g (yield: 59%) of [(hydroxy-4 butyl-1]-3-3H-benzotriazine-1,2,3 one-4 are obtained. Melting point=47°–49.5° C.

I.R. $\bar{\nu}(C=O) = 1665$ cm$^{-1}$.

(b) [[(Methyl-4 benzensulfonyl)-4 butyl]-1]-3-3H-benzotriazine-1,2,3 one-4

7.3 g (38 m. moles) of 4-methylbenzenesulfonyl chloride are added by portions to a solution, cooled to 0° C., of 4.2 g (18 m. moles) of [(hydroxy-4 butyl)-1]-3-3H-benzotriazine-1,2,3 one-4 in 90 cc of pyridine. The mixture is stirred 4 hours at 0° C. then left 4 days at this temperature. It is then thrown into 750 cc of ice water. The precipitate is filtered, washed with water and dried. Then are obtained 4.9 g (yield 69%) of [[(methyl-4 benzensulfonyl-4-butyl]- 1]-3-3H-benzotriazine-1,2,3 one-4, melting at 80°–80° C. and they used without any other purification.

(c) [[(Chloro-3 phenyl)-4 piperazinyl-1]-4 butyl]-3-3H-benzotriazine-1,2,3 one-4

A mixture of 17.5 g (46.9 m. moles) of [[(methyl-4 benzene sulfonyl)-4 butyl]-1]-3-3H-benzotriazine-1,2,3 one-4, 9.2 g (46.9 m. moles) of 1-(3-chlorophenyl piperazine, 7.1 g (51.4 m. moles) of potassium carbonate and 190 cc of N,N-dimethylformamide is stirred 7 hours at ambient temperature then 3 hours at 80° C. After cooling, the reactive medium is diluted with 1 liter of water. The precipitate formed is filtered, washed with water and dried. It is filtered on a silica column (eluent: 1:1 hexane-ethyl acetate)then recrystallized in a hexane-ethyl acetate mixture. Thus 9.9 g (yield: 53%) [[(chloro-3 phenyl)-4 piperazinyl-1]-4 butyl]-3-3H-benzotriazine-1,2,3 one-4 are obtained. Melting point=107.5°–109.5° C.

| Percentage analysis $C_{21}H_{24}ClN_5O$ M = 397.90 | | | | |
|---|---|---|---|---|
| | C % | H % | Cl % | N % |
| Calculated | 63.39 | 6.08 | 8.91 | 17.60 |
| Found | 63.38 | 6.12 | 8.78 | 17050 |

I.R. $\bar{\nu}(C=O) = 1685$ cm$^{-1}$.

What is claimed is:

1. [(Phenyl-4 piperazinyl-1)-3alkyl]-3-3H-benzo- and thieno-triazine-1,2,3 characterized by the formula:

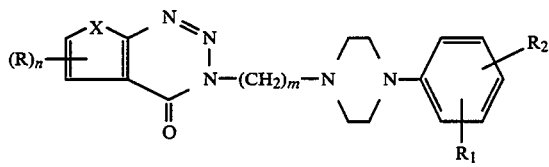

in which m is 2, 3 or 4, X is the vinylene group —CH=CH— or a sulfur atom; $R_1$ and $R_2$ can be alike or different and are hydrogen, a halogen, a lower alkyl radical, lower alkoxy radical or trifluoromethyl radical; when X is —CH=CH—, n is 0, 1 or 2 and R is hydrogen, a halogen, a lower alkyl radical, lower alkoxy radical, or the nitro group; when X is a sulfur atom, R is hydrogen or constitutes a —(CH$_2$)$_4$— chain between the two open positions of the thiophenic ring; and their salts of pharmaceutically acceptable inorganic or organic acids.

2. [(Phenyl-4 piperazinyl-1)-3 alkyl]-3-3H-benzo- and thieno-triazine-1,2,3 one-4 in accordance with claim 1 wherein $R_1$ and $R_2$ can be alike or different and are hydrogen or a halogen; and their salts of pharmaceutically acceptable inorganic or organic acids.

3. [(Phenyl-4 piperazinyl-1)-3 alkyl]-3-3H-benzo- and thieno-triazine-1,2,3 ones-4 in accordance with claim 1 wherein $R_1$ is a chlorine atom located in the meta position in relation to the piperazine and $R_2$ is hydrogen; and their salts of pharmaceutically acceptable inorganic or organic acids.

4. A composition comprising as active principle an amount effective for anti-depressant activity of a [(phenyl-4 piperazino-1)-3 alkyl]-3-3H-benzo- or thieno-triazine-1, 2, 3 one-4 having the formula

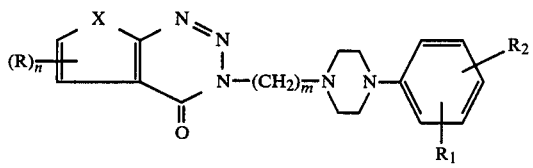

in which m equals 2, 3 or 4; X is the vinylene group —CH=CH— or a sulfur atom; $R_1$ and $R_2$ can be alike or different and are hydrogen, a halogen, a lower alkyl radical, a lower alkoxy radical or a trifluoromethyl radical; when X equals —CH=CH—, n is 0, 1 or 2 and R is hydrogen, a halogen, a lower alkyl radical, a lower alkoxyl radical or the nitro group radical; when X is a sulfur atom R is hydrogen or constitutes a —(CH$_2$)$_4$— between the two open positions of the thiophenic ring; or a salt of a pharmaceutically acceptable inorganic or organic acid thereof; together with a pharmaceutically acceptable carrier.

5. A compound according to claim 1 which is [[(Chloro-3-phenyl)-1-piperazinyl-1]-3-propyl]-3-methyl-6-3H-benzotriazine-1,2,3 one-4, hydrochloride.

6. A compound according to claim 1 which is [[(Chloro-3-phenyl)-4-piperazinyl-1]-3-3H]-benzotriazine-1,2,3 one-4, hydrochloride.

* * * * *